(12) United States Patent
Hayakawa et al.

(10) Patent No.: US 11,266,301 B2
(45) Date of Patent: Mar. 8, 2022

(54) INSERTING APPARATUS

(71) Applicant: OLYMPUS CORPORATION, Tokyo (JP)

(72) Inventors: Fumitoshi Hayakawa, Machida (JP); Akihiro Kato, Hino (JP); Kazuki Minamimoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 100 days.

(21) Appl. No.: 16/939,371

(22) Filed: Jul. 27, 2020

(65) Prior Publication Data

US 2020/0352418 A1 Nov. 12, 2020

Related U.S. Application Data

(63) Continuation of application No. PCT/JP2018/032171, filed on Aug. 30, 2018.

(30) Foreign Application Priority Data

Jan. 31, 2018 (JP) .............................. JP2018-015050

(51) Int. Cl.
*A61B 1/00* (2006.01)
*A61B 1/01* (2006.01)
(Continued)

(52) U.S. Cl.
CPC .......... *A61B 1/00098* (2013.01); *A61B 1/018* (2013.01); *A61B 1/0011* (2013.01); *A61B 1/00101* (2013.01)

(58) Field of Classification Search
CPC ............ A61B 1/00098; A61B 1/00101; A61B 1/0011; A61B 1/00137; A61B 1/0018; G02B 23/24
See application file for complete search history.

(56) References Cited

U.S. PATENT DOCUMENTS 8,421,838 B2 * 4/2013 Yamaguchi .......... G02B 26/123
347/238
10,149,604 B2 * 12/2018 Hiraoka .................. A61B 1/00
(Continued)

FOREIGN PATENT DOCUMENTS

EP 3308715 A1 4/2018
EP 3308715 A4 * 2/2019 ............... A61B 8/12
(Continued)

OTHER PUBLICATIONS

International Search Report dated Nov. 20, 2018 issued in PCT/JP2018/032171.

*Primary Examiner* — Bayan Salone
(74) *Attorney, Agent, or Firm* — Scully, Scott, Murphy & Presser, P.C.

(57) ABSTRACT

An inserting apparatus of the present invention includes a base provided in an insertion section, a first recess provided in the base, an opening forming surface formed around the first recess, a movable member configured to move in the first recess, a tabular lid member configured to close an opening of the first recess, a second recess provided in the lid member, a wall surface provided on the base, and opposed to at least a part of a side surface of the lid member in a state in which the contact surface is in contact with the opening forming surface, a fixing resin fixing the lid member to the base, and one or a plurality of protrusions provided on the side surface, having thickness smaller than thickness in the side surface of the lid member, and projecting toward the wall surface.

13 Claims, 13 Drawing Sheets

(51) Int. Cl.
*G02B 23/24* (2006.01)
*A61B 1/018* (2006.01)

(56) References Cited

U.S. PATENT DOCUMENTS

| | | | | |
|---|---|---|---|---|
| 10,299,660 | B2* | 5/2019 | Hosogoe | ................ A61B 10/04 |
| 2011/0109713 | A1* | 5/2011 | Yamaguchi | ............ G02B 26/10 |
| | | | | 347/224 |
| 2016/0206180 | A1* | 7/2016 | Hosogoe | ............... A61B 1/0057 |
| 2018/0092512 | A1* | 4/2018 | Hiraoka | ............. A61B 1/00098 |

FOREIGN PATENT DOCUMENTS

| | | | | |
|---|---|---|---|---|
| JP | H02-40936 A | | 2/1990 | |
| JP | 2002-017663 A | | 1/2002 | |
| JP | 2002017663 A | * | 1/2002 | |
| JP | 2005-304586 A | | 11/2005 | |
| JP | 2005304586 A | * | 11/2005 | ......... A61B 1/00098 |
| JP | 2007-136044 A | | 6/2007 | |
| JP | 2007136044 A | * | 6/2007 | ......... A61B 1/00098 |
| JP | 2011-124541 A | | 6/2011 | |
| JP | 2011124541 A | * | 6/2011 | ........... G02B 26/123 |
| JP | 2011224277 A | * | 11/2011 | |
| JP | 2016-131578 A | | 7/2016 | |
| JP | 2016131578 A | * | 7/2016 | ......... A61B 1/00098 |
| WO | WO 2016/199694 A1 | | 12/2016 | |
| WO | WO-2016199694 A1 | * | 12/2016 | ......... A61B 1/00098 |
| WO | WO 2017/179293 A1 | | 10/2017 | |
| WO | WO-2017179293 A1 | * | 10/2017 | ......... A61B 1/00142 |

\* cited by examiner

INSERTING APPARATUS

CROSS REFERENCE TO RELATED APPLICATION

This application is a continuation application of PCT/JP2018/032171 filed on Aug. 30, 2018 and claims benefit of Japanese Application No. 2018-15050 filed in Japan on Jan. 31, 2018, the entire contents of which are incorporated herein by this reference.

BACKGROUND OF THE INVENTION

1. Field of the Invention

The present invention relates to an inserting apparatus including an insertion section inserted into a subject and a movable member provided in the insertion section.

2. Description of the Related Art

As an inserting apparatus including an insertion section inserted into a subject such as an endoscope or a medical treatment instrument, there is a type including a movable member in the insertion section. For example, Japanese Patent Application Laid-Open Publication No. 2007-136044 discloses an endoscope including a raising lever, which is a movable member, and a raising base in an insertion section.

In the endoscope disclosed in Japanese Patent Application Laid-Open Publication No. 2007-136044, the raising lever is disposed in a lever housing section, which is a concave space formed in a distal end portion main body of the insertion section. In the endoscope disclosed in Japanese Patent Application Laid-Open Publication No. 2007-136044, the lever housing section is closed by a thin tabular cover.

Since the inserting apparatus is repeatedly used, improvement of resistance against physical shocks is required for the inserting apparatus. For example, for the inserting apparatus including the cover that closes the lever housing section disclosed in Japanese Patent Application Laid-Open Publication No. 2007-136044, it is required to improve strength for fixing the cover.

SUMMARY OF THE INVENTION

An inserting apparatus according to an aspect of the present invention includes: a base provided in an insertion section inserted into a subject; a first recess recessed on a surface of the base; an opening forming surface formed around an opening of the first recess on the surface of the base; a movable member configured to move with respect to the base in the first recess, a part of the movable member projecting from the opening of the first recess; a tabular lid member including a contact surface larger than the opening of the first recess and in contact with the opening forming surface, the lid member closing the opening of the first recess when the contact surface comes into contact with the opening forming surface; a second recess recessed on the contact surface of the lid member, the second recess forming a housing space including the movable member when the second recess is connected to the first recess in a state in which the lid member closes the opening of the first recess; a wall surface provided on the base, erected toward an outer side of the base from the opening forming surface, and opposed to at least a part of a side surface of the lid member in a state in which the contact surface is in contact with the opening forming surface; a fixing resin disposed at least in a gap between the side surface of the lid member and the wall surface in the state in which the contact surface is in contact with the opening forming surface, the fixing resin fixing the lid member to the base; and one or a plurality of protrusions provided in one of the side surface of the lid member and the wall surface, having thickness smaller than thickness in the side surface of the lid member, and projecting from the one of the side surface of the lid member and the wall surface toward another of the side surface of the lid member and the wall surface.

An inserting apparatus according to another aspect of the present invention includes: a base provided in an insertion section inserted into a subject; a first recess recessed on a surface of the base; an opening forming surface formed around an opening of the first recess on the surface of the base; a movable member configured to move with respect to the base in the first recess; a lid member including a contact surface in contact with the opening forming surface, the lid member closing the opening of the first recess; a second recess provided in the lid member, the second recess covering the movable member when the second recess is connected to the first recess in a state in which the opening of the first recess is closed; a wall surface provided on the base, erected toward an outer side of the base from the opening forming surface, and opposed to at least a part of a side surface of the lid member; a fixing resin that fixes the lid member to the base; and one or a plurality of protrusions provided in one of the side surface of the lid member and the wall surface and projecting from the one of the side surface of the lid member and the wall surface toward another of the side surface of the lid member and the wall surface, wherein the opening forming surface is formed from a surface formed on a side surface of the base and extending in a longitudinal axis direction of the insertion section, the movable member moves within a predetermined moving range in the longitudinal axis direction with respect to the base, at least one of both ends in the moving range is decided by a position where the movable member is in contact with a restricting section that is a part of a sidewall of the first recess, an opening width in the longitudinal axis direction of the second recess is larger than an opening width of the first recess, and a sidewall of the second recess is disposed to be separated in the longitudinal axis direction from the movable member in a contact state with the restricting section.

DETAILED DESCRIPTION OF THE PREFERRED EMBODIMENT

A preferred embodiment of the present invention is explained below with reference to the drawings. Note that, in figures used for the following explanation, scales are differentiated for each of components in order to show the components in recognizable sizes on the drawings. The present invention is not limited to only quantities of the components, shapes of the components, ratios of the sizes of the components, and relative positional relations among the components described in these figures.

Figure 1:
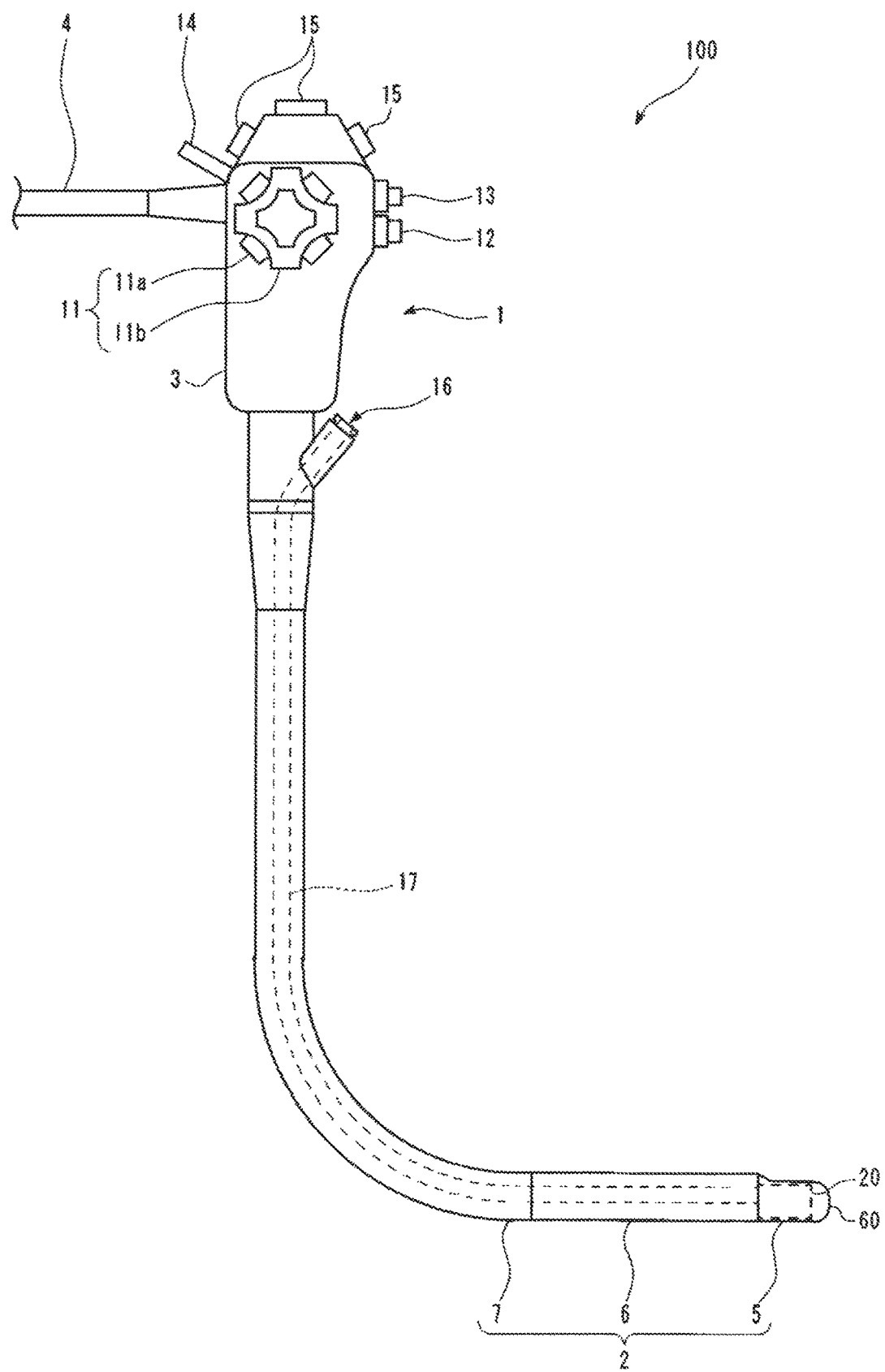
FIG. 1 is a diagram showing a schematic configuration of a side-viewing endoscope.

FIG. 1 is a diagram showing a schematic configuration of an inserting apparatus 100. The inserting apparatus 100 in the present embodiment includes an inserting apparatus main body 1 and a distal end cover 60. In the present embodiment, as an example, the inserting apparatus 100 is an endoscope including an insertion section 2 inserted into a human body, which is a subject, and is, more specifically, a side-viewing endoscope for duodenum.

The inserting apparatus main body 1 includes the insertion section 2 inserted into the subject, an operation section 3 provided on a proximal end side of the insertion section 2, and a universal cord 4 extended from the operation section 3.

In the operation section 3, a bending operation apparatus 11, an air/water feeding button 12, a suction button 13, a raising base operation lever 14, and an operation switch 15 are provided. The operation switch 15 is an electronic switch for operating an image pickup apparatus 42 (not shown in FIG. 1) provided in the insertion section 2.

In the operation section 3, a treatment instrument insertion port 16 for introducing a not-shown treatment instrument into a body is provided. A proximal end side of a channel tube 17 is connected to the treatment instrument insertion port 16. A distal end side of the channel tube 17 is opened at a distal end portion 5 of the insertion section 2.

The insertion section 2 is configured by concatenating the distal end portion 5 disposed at a distal end, a bendable bending section 6 disposed on a proximal end side of the distal end portion 5, and a flexible tube section 7 having flexibility that connects a proximal end side of the bending section 6 and the operation section 3. The distal end cover 60 is attached to the distal end portion 5. Details of configurations of the distal end portion 5 and the distal end cover 60 are explained below.

The bending section 6 bends in an upward direction or a downward direction according to rotation of an upper and lower bending knob 11a of the bending operation apparatus 11 provided in the operation section 3 and bends in a left direction or a right direction according to rotation of a left and right bending knob 11b.

A raising base operation wire 18 (not shown in FIG. 1) is inserted through the insertion section 2. The raising base operation wire 18 advances and retracts in a longitudinal direction according to swinging of the raising base operation lever 14. In other words, the raising base operation lever 14 is an operation member for a user to operate an apparatus that pushes and pulls the raising base operation wire 18 inserted through the insertion section 2. A distal end of the raising base operation wire 18 is connected to a movable member 51 (not shown in FIG. 1) explained below provided in the distal end portion 5.

Figure 2:
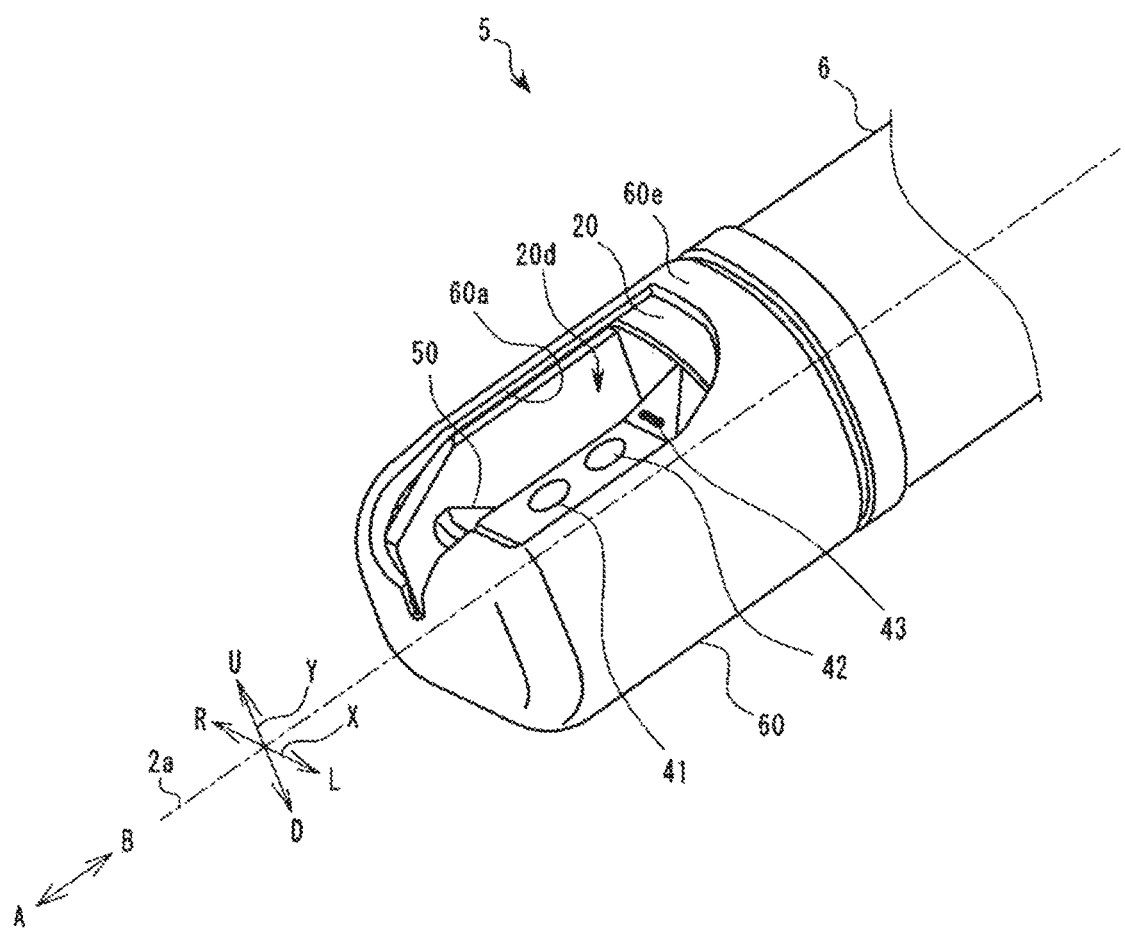
FIG. 2 is a perspective view of a distal end portion of an insertion section.
Figure 3:
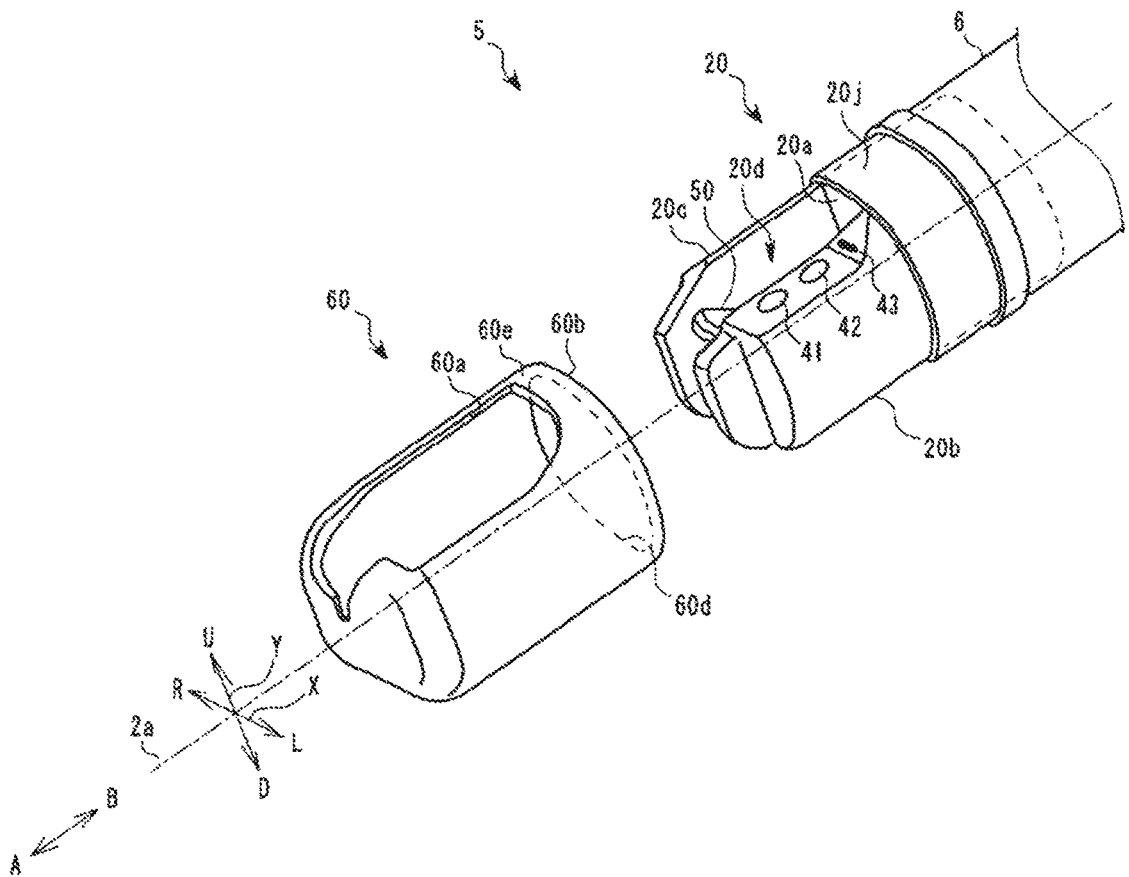
FIG. 3 is a perspective view showing a distal end cover and a distal end member in a separated state.

FIG. 2 is a perspective view of the distal end portion 5. As shown in FIG. 2, the distal end cover 60 is attached to the distal end portion 5. The distal end cover 60 is a sheath-like member that covers a predetermined outer surface of the distal end portion 5. The distal end cover 60 is detachably attachable to the distal end portion 5. FIG. 3 is a perspective view showing the distal end cover 60 and the distal end portion 5 in a separated state.

In the present embodiment, as an example, the distal end cover 60 is formed of resin having low elasticity compared with rubber and the like and easily plastically deformed or fractured among kinds of resin such as polyethylene or polypropylene. In the distal end cover 60 in the present embodiment, irreversible deformation and fracture occur when the distal end cover 60 is detached from the distal end portion 5 after being attached to the distal end portion 5 and cannot be reused. FIG. 3 shows the distal end cover 60 in a state in which the distal end cover 60 has not been attached yet to the distal end portion 5 (an unused state).

A configuration of the distal end portion 5 is explained. Note that, in the following explanation, an axis in the longitudinal direction of the elongated insertion section 2 is referred to as longitudinal axis 2a. A direction toward a distal end side of the insertion section 2 along the longitudinal axis 2a is referred to as distal end direction A. The opposite direction of the distal end direction A is referred to as proximal end direction B. Two linear axes orthogonal to each other on a plane orthogonal to the longitudinal axis 2a are defined as an X axis and a Y axis. A direction toward one side along the X axis is referred to as right direction R. The opposite direction of the right direction R is referred to as left direction L. A direction toward one side along the Y axis is referred to as upward direction U. The opposite direction of the upward direction U is referred to as downward direction D. The X axis and the Y axis are substantially parallel to a bending direction of the bending section 6. In the present embodiment, as an example, when viewed from the proximal end side toward the distal end side along the longitudinal axis 2a and when the X axis is horizontal, it is assumed that a right side is the right direction R and an upper side is the upward direction U.

Figure 4:
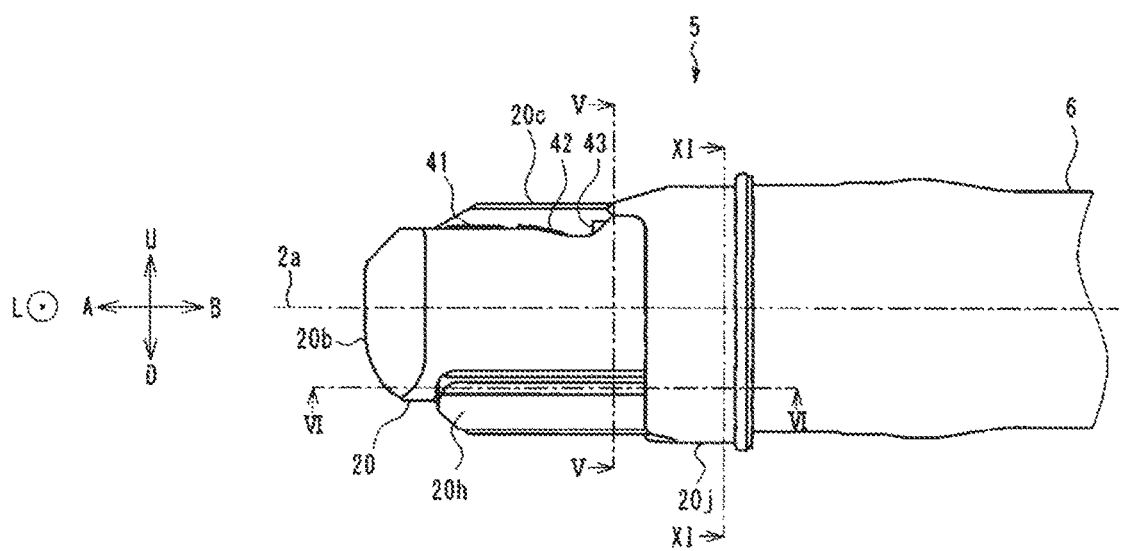
FIG. 4 is a diagram showing a left side surface of the distal end portion in a state in which the distal end cover is not attached.
Figure 5:
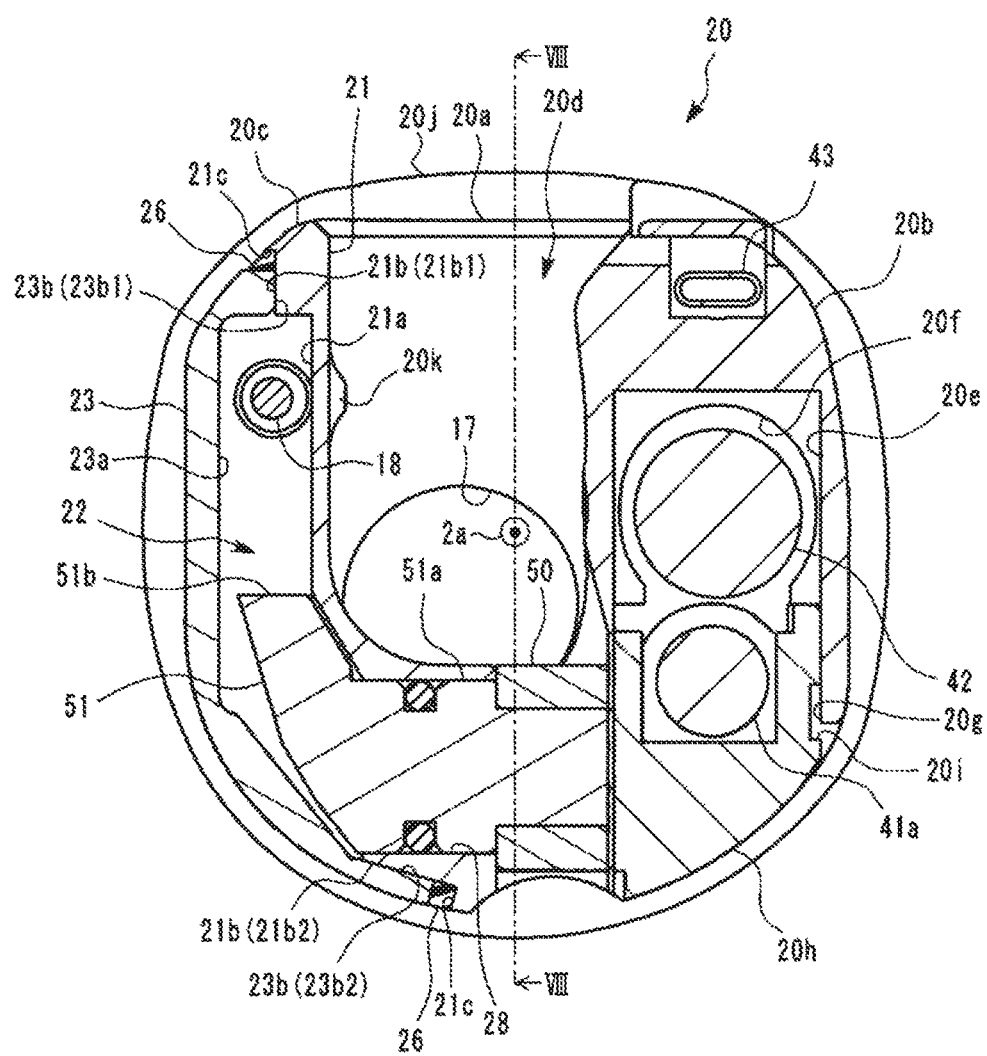
FIG. 5 is a V-V sectional view of FIG. 4.
Figure 5:
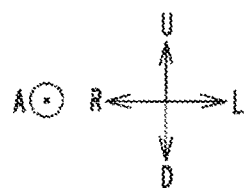
Figure 6:
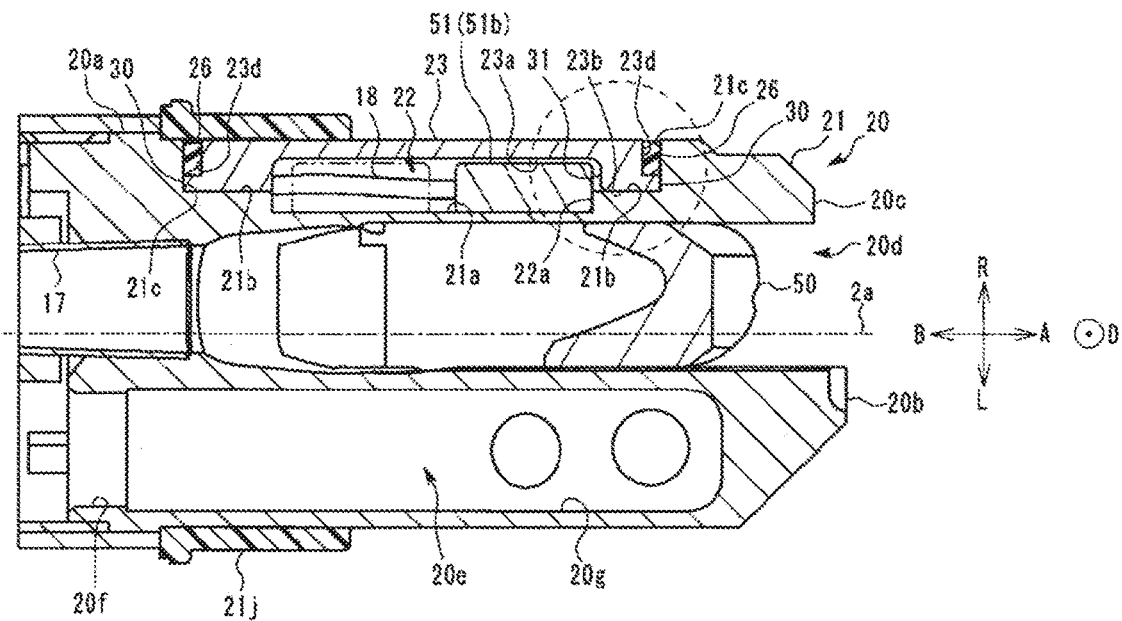
FIG. 6 is a VI-VI sectional view of FIG. 4.
Figure 7:
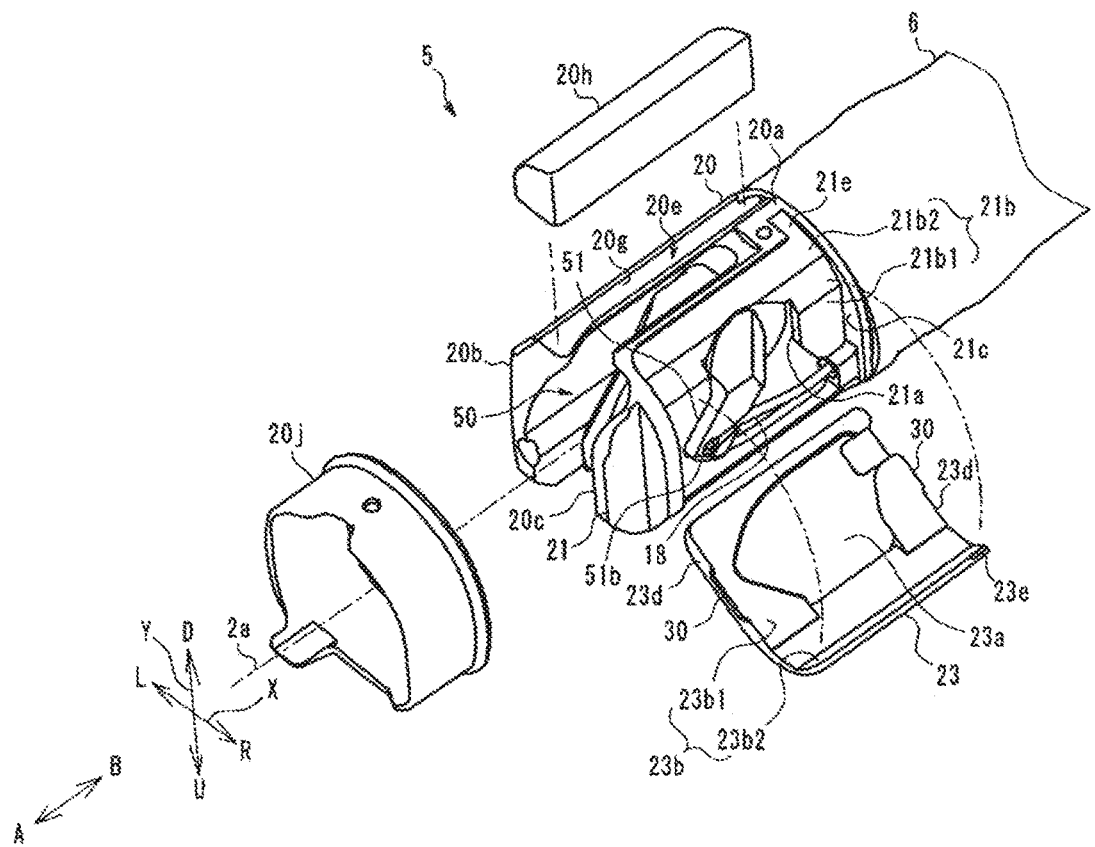
FIG. 7 is an exploded perspective view of the distal end member.

FIG. 4 is a diagram showing a left side surface of the distal end portion 5 in a state in which the distal end cover 60 is not attached. FIG. 5 is a V-V sectional view of FIG. 4. FIG. 6 is a VI-VI sectional view of FIG. 4. FIG. 7 is an exploded perspective view of a distal end member 20.

As shown in FIG. 3, the distal end portion 5 includes the distal end member 20 and an insulating section 20j made of resin or ceramic having electric insulation. The distal end member 20 includes a base portion 20a fixed to a distal end of the bending section 6, a first arm section 20b and a second arm section 20c, which are a pair of arm sections projecting in the distal end direction A from the base portion 20a, and a raising base housing space 20d, which is a space formed between the first arm section 20b and the second arm section 20c. An outer shape of the base portion 20a is a substantially columnar shape. An outer circumference of the base portion 20a is covered by the annular insulating section 20j.

The first arm section 20b and the second arm section 20c are disposed such that the raising base housing space 20d, which is the space thrilled between the first arm section 20b and the second arm section 20c, is opened in three directions of the upward direction U, the downward direction D, and the distal end direction A. In other words, the first arm section 20b and the second arm section 20c are arrayed in a direction along the X axis with the raising base housing space 20d in between. In the present embodiment, as an example, the first arm section 20b is disposed on the left direction L side of the raising base housing space 20d and the second arm section 20c is disposed on the right direction R side of the raising base housing space 20d.

An illumination lens 41, an image pickup apparatus 42, and a cleaning nozzle 43 are disposed on an upper surface in the upward direction U in an outer circumferential surface of the first arm section 20b. The illumination lens 41 is a lens for emitting illumination light toward an object of the image pickup apparatus 42. The illumination light is guided from a light emitting apparatus to the illumination lens 41 via an optical fiber cable 41a inserted through the insertion section 2. The light emitting apparatus may be disposed in the inserting apparatus 100 or may be disposed in an external apparatus connected to the inserting apparatus 100.

A visual field of the image pickup apparatus 42 is generally centered on the upward direction U. In other words, the image pickup apparatus 42 catches a side direction of the insertion section 2 in the visual field. The cleaning nozzle 43 is a part that jets fluid toward the illumination lens 41 and the image pickup apparatus 42.

As shown in FIG. 5, an image pickup apparatus housing space 20e is formed on an inside of the first arm section 20b. A distal end portion of the optical fiber cable 41a and the image pickup apparatus 42 are disposed in the image pickup apparatus housing space 20e.

The image pickup apparatus housing space 20e communicates with an internal space of the bending section 6 via a through-hole 20f that pierces through the base portion 20a. The distal end portion of the optical fiber cable 41a and the image pickup apparatus 42 are inserted into the image pickup apparatus housing space 20e through the through-hole 20f.

The image pickup apparatus housing space 20e includes an opening section 20g opened on a lower surface in the downward direction D of the first arm section 20b as shown in FIG. 7. The opening section 20g is closed by a plug body 20h fit into the opening section 20g. The plug body 20h is fixed in the opening section 20g by an adhesive. As shown in FIG. 5, a claw 20i for catching a tool, for example, when the plug body 20h is pulled out from the opening section 20g during maintenance of the inserting apparatus 100 is formed in the plug body 20h.

As explained in detail below, a housing space 22, in which the movable member 51 is disposed, is provided in the second arm section 20c. The movable member 51 is a member that transmits a movement of the raising base operation wire 18 to a raising base (forceps elevator) 50.

The distal end cover 60 is a sheath-like member closed on the distal end direction A side and opened on the proximal end direction B side. An opening provided on the proximal end direction B side of the distal end cover 60 is referred to as insertion port 60d. When the distal end cover 60 is attached to the distal end portion 5, the distal end portion 5 is inserted into the distal end cover 60 through the insertion port 60d.

The distal end cover 60 includes an opening section 60a that exposes the raising base housing space 20d in only the upward direction U in a state in which the distal end cover 60 is attached to the distal end portion 5. In a state in which the distal end cover 60 is attached to the distal end member 20, the illumination lens 41, the image pickup apparatus 42, and the cleaning nozzle 43 are also exposed in the upward direction U via the opening section 60a.

On an outer surface of the distal end cover 60, the opening section 60a is not connected to the insertion port 60d. Accordingly, an annular section 60e, an entire circumference of which is annularly connected around the longitudinal axis 2a, is formed at a proximal end 60b of the distal end cover 60. In the state in which the distal end cover 60 is attached to the distal end member 20, the annular section 60e fits with an outer circumference of the insulating section 20j.

Configurations of the housing space 22 provided in the second arm section 20c of the distal end member 20 and the movable member 51 disposed in the housing space 22 are explained.

Figure 8:
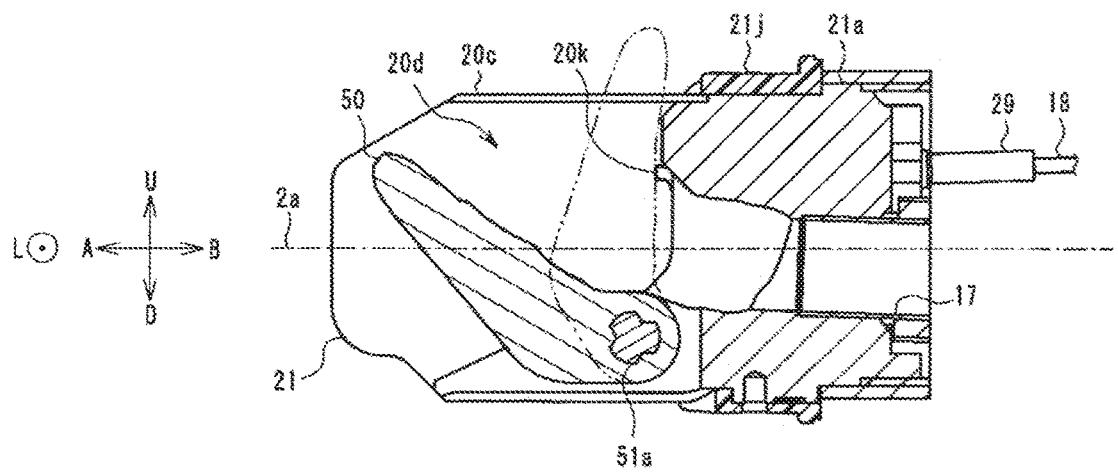
FIG. 8 is a VIII-VIII sectional view of FIG. 5.
Figure 9:
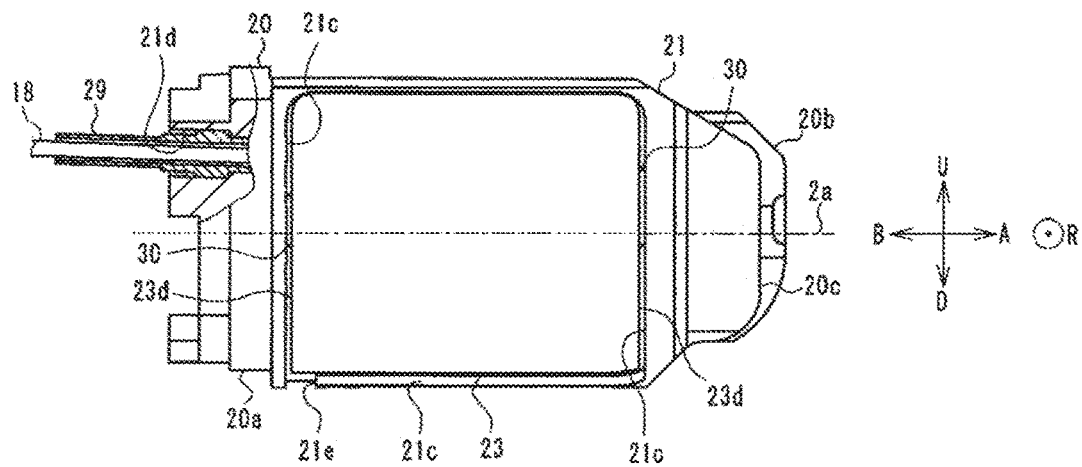
FIG. 9 is a partial sectional view showing a right side surface of the distal end member.
Figure 10:
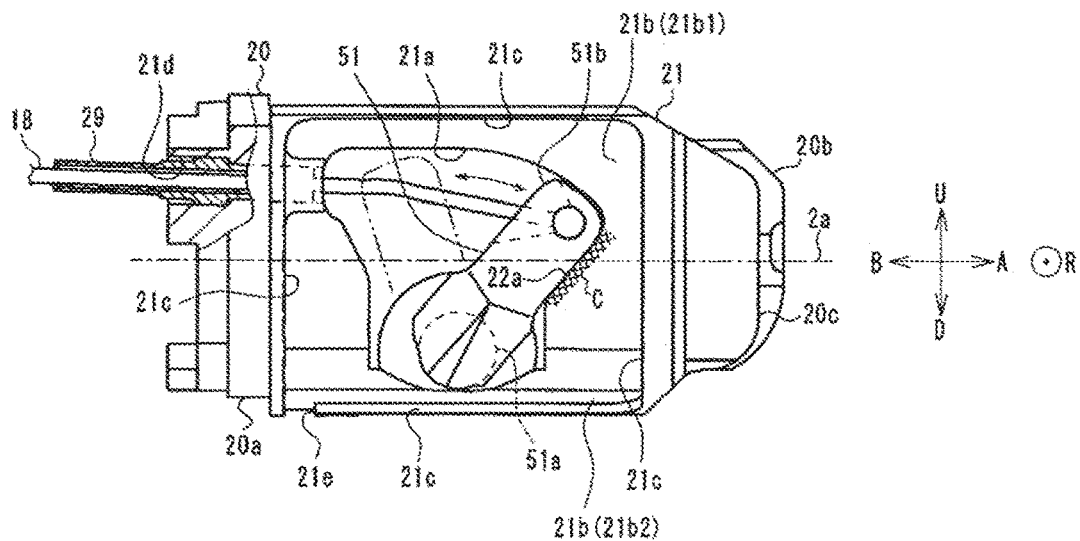
FIG. 10 is a diagram showing the right side surface of the distal end member in a state in which a lid member is detached.
Figure 11:
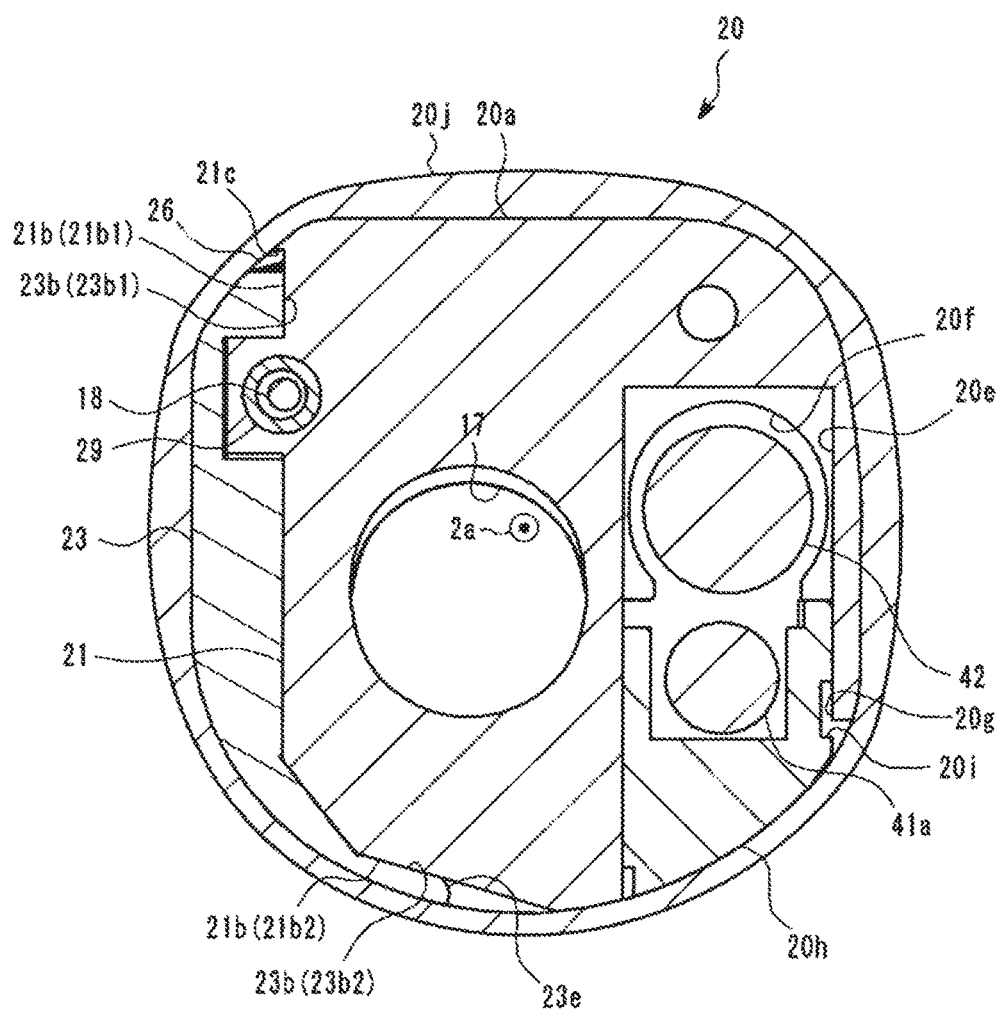
FIG. 11 is a XI-XI sectional view of FIG. 4.
Figure 11:
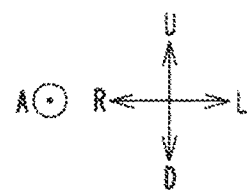
Figure 12:
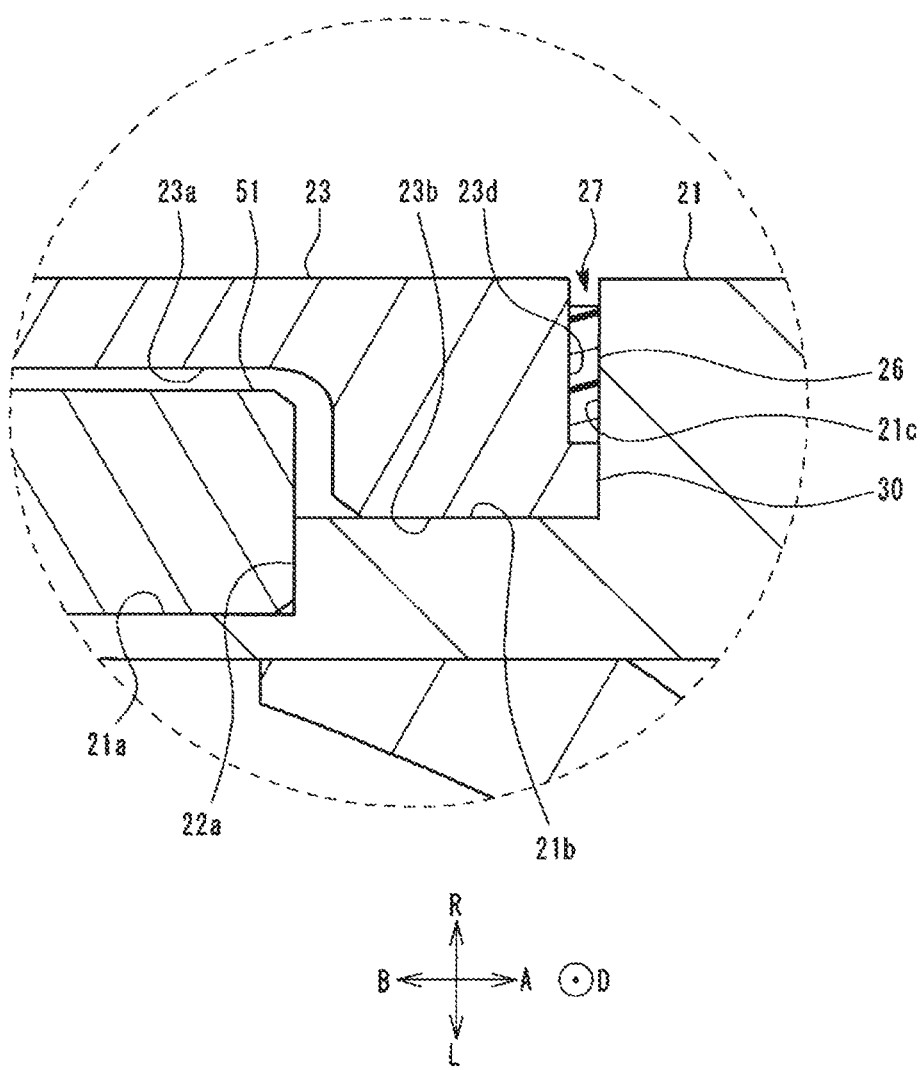
FIG. 12 is an enlarged view of a portion surrounded by a circle drawn by a broken line in FIG. 6.

FIG. 8 is a VIII-VIII sectional view of FIG. 5. FIG. 9 is a partial sectional view showing a right side surface of the distal end member 20. FIG. 10 is a diagram showing the right side surface of the distal end member 20 in a state in which a lid member 23 is detached. FIG. 11 is a XI-XI sectional view of FIG. 4. FIG. 12 is an enlarged view of a portion surrounded by a circle drawn by a broken line in FIG. 6.

As shown in FIG. 5, FIG. 6, and FIG. 7, the second arm section 20c is configured by a base section 21 integral with the distal end member 20 and the lid member 23 bonded and fixed to the base section 21 by a fixing resin 26. In the present embodiment, the lid member 23 is fixed to a left side surface of the base section 21. The housing space 22 is configured by a first recess portion 21a and a second recess portion 23a respectively recessed on surfaces opposed to each other of the base section 21 and the lid member 23.

More specifically, the base section 21 includes a first recess portion 21a, an opening forming surface 21b, and a wall surface section 21c. The first recess portion 21a is opened in the opening forming surface 21b in a surface of the base section 21. In other words, the opening forming surface 21b is a surface formed to surround a circumference of an opening of the first recess portion 21a.

A shape of the opening forming surface 21b is not particularly limited and, for example, may be configured by a single plane, may be configured by a plurality of planes, or may be configured by a curved surface.

In the present embodiment, as an example, as shown in FIG. 5 and FIG. 11, the opening forming surface 21b includes a pair of planes 21b1 and 21b2 substantially parallel to the longitudinal axis 2a and disposed at angles at which the pair of planes 21b1 and 21b2 cross each other. The pair of planes 21b1 and 21b2 faces different directions on a surface of the columnar base section 21 such that a crossing line of the pair of planes 21b1 and 21b2 is formed as a ridgeline convex to an outer side.

The opening forming surface 21b including the pair of planes 21b1 and 21b2 is formed in a shape bent in a ridge shape in a cross section orthogonal to the longitudinal axis 2a.

The wall surface section 21c is erected toward an outer side of the base section 21 from the opening forming surface 21b. The wall surface section 21c is explained below.

The lid member 23 is a tabular member and includes a second recess portion 23a, a contact surface 23b, and a protrusion 30. The contact surface 23b is a surface in contact with the opening forming surface 21b. The contact surface 23b is larger than the opening of the first recess portion 21a and is in contact with the opening forming surface 21b over an entire circumference of the opening of the first recess portion 21a. Therefore, in a state in which the contact surface 23b is in contact with the opening forming surface 21b, the opening of the first recess portion 21a is closed by the lid member 23.

Since an outer circumferential portion of the second recess portion 23a, that is, a portion near a side surface 23d is thicker than a center portion where the second recess portion 23a is formed, the lid member 23 has higher strength compared with plate having thickness equivalent to thickness in the center portion.

The contact surface 23b has a shape adhering to the opening forming surface 21b in order to close the first recess portion 21a. Specifically, in the present embodiment, since the opening forming surface 21b has the shape bent in the ridge shape in the cross section parallel to the longitudinal axis 2a, the contact surface 23b has a shape bent in a trough shape according to the bending of the opening forming surface 21b. In other words, the contact surface 23b includes a pair of planes 23b1 and 23b2 parallel to the pair of planes 21b1 and 21b2 of the opening forming surface 21b.

Since the opening forming surface 21b on the base section 21 side has the ridge shape and the contact surface 23b on the lid member 23 side has the trough shape, the lid member 23 is positioned in a circumferential direction around the longitudinal axis 2a with respect to the base section 21 by bringing the contact surface 23b into contact with the opening forming surface 21b. In the present embodiment, the positioning of the lid member 23 in the circumferential direction around the longitudinal axis 2a with respect to the base section 21 is positioning in the upward direction U and the downward direction D generally along the Y axis.

The second recess portion 23a is opened in the contact surface 23b. In other words, a circumference of an opening of the second recess portion 23a is surrounded by the contact surface 23b. The second recess portion 23a is connected to the first recess portion 21a in a state in which the lid member 23 closes the opening of the first recess portion 21a.

As explained above, the housing space 22 is formed by bonding the base section 21 and the lid member 23 such that the first recess portion 21a provided in the base section 21 and the second recess portion 23a provided in the lid member 23 face each other. Therefore, on a sidewall surface of the housing space 22, a boundary line between the base section 21 and the lid member 23 is present in a position separated from respective bottom surfaces of the first recess portion 21a and the second recess portion 23a.

The sidewall surface of the housing space 22 is a surface excluding the bottom surfaces of the first recess portion 21a and the second recess portion 23a in an inner surface of the housing space 22. In other words, the sidewall surface of the housing space 22 is configured by sidewalls of the first recess portion 21a and the second recess portion 23a. The boundary line is a mating surface of the base section 21 and the lid member 23, that is, the opening forming surface 21b and the contact surface 23b appearing on the sidewall surface of the housing space 22. In the present embodiment, the mating surface of the base section 21 and the lid member 23 is substantially parallel to the longitudinal axis 2a.

The wall surface section 21c provided in the base section 21 and the protrusion 30 provided in the lid member 23 are explained.

The wall surface section 21c is erected toward the outer side of the base section 21 from the opening forming surface 21b. The wall surface section 21c has a surface opposed to at least a part of the side surface 23d of the lid member 23 in a state in which the contact surface 23b is in contact with the opening forming surface 21b.

The wall surface section 21c in the present embodiment is disposed to surround a circumference of the lid member 23 at a predetermined distance apart from the side surface 23d. In the present embodiment, the wall surface section 21c is a sidewall surface of a recess portion formed on a surface of the base section 21 and having a shape, on an inner side of which the lid member 23 is fit. The opening forming surface 21b corresponds to a bottom surface of the recess portion.

The protrusion 30 projects toward the wall surface section 21c from a part of the side surface 23d of the lid member 23. As shown in FIG. 6 and FIG. 12, the protrusion 30 has thickness smaller than thickness in the side surface 23d of the lid member 23. The protrusion 30 is separated in a thickness direction from at least one of the contact surface 23b of the lid member 23 and an outer surface 23f on the opposite side of the contact surface 23b. In the present embodiment shown in FIG. 12, the protrusion 30 is separated from the outer surface 23f of the lid member 23. The protrusion 30 is in contact with the wall surface section 21c, whereby the side surface 23d in a portion where the protrusion 30 is provided is prevented from adhering to the wall surface section 21c. A gap 27 having a predetermined width is formed between the side surface 23d and the wall surface section 21c.

In the present embodiment, as an example, the lid member 23 generally has a rectangular shape. The side surface 23d of the lid member 23 includes a pair of surfaces substantially parallel to the longitudinal axis 2a and a pair of surfaces substantially orthogonal to the longitudinal axis 2a. The lid member 23 includes a plurality of protrusions 30 projecting in both directions the distal end direction A and the proximal end direction B) along the longitudinal axis 2a from a pair of side surfaces 23d substantially parallel to the longitudinal axis 2a.

The wall surface section 21c provided in the base section 21 is disposed to hold the lid member 23 from both the directions along the longitudinal axis 2a. Therefore, in the present embodiment, the protrusion 30 is in contact with the wall surface section 21c, whereby the lid member 23 is positioned in the longitudinal axis 2a direction with respect to the base section 21.

The lid member 23 is positioned in a direction (a circumferential direction) orthogonal to the longitudinal axis 2a with respect to the base section 21 by bringing the contact surface 23b into contact with the opening forming surface 21b as explained above. Therefore, in the present embodiment, when the lid member 23 is bonded to the base section 21, the lid member 23 can be positioned on the surface of the base section 21 by bringing the contact surface 23b into contact with the opening forming surface 21b and bringing the protrusion 30 into contact with the wall surface section 21c.

At this time, the gap 27 having a groove shape is formed between the lid member 23 and the wall surface section 21c surrounding the circumference of the lid member 23. Since the protrusion 30 is thinner than the wall surface section 21c, the gap 27 formed around the lid member 23 continues without being cut along an outer circumference of the contact surface 23b of the lid member 23.

A fixing resin 26 before curing is poured into the gap 27 formed between the lid member 23 and the wall surface section 21c and, thereafter, the fixing resin 26 is cured, whereby the lid member 23 is bonded and fixed to the base section 21. In the present embodiment, since the fixing resin 26 can be closely disposed without being cut along the outer circumference of the contact surface 23b of the lid member 23. Therefore, it is possible to surely and firmly fix the lid member 23 to the base section 21.

In the present embodiment, as shown in FIG. 7 and FIG. 11, in a part of a corner where the contact surface 23b of the lid member 23 and the side surface 23d cross, a chamfered section 23e formed by cutting out the corner is formed. A cutout 21e is formed in the wall surface section 21c opposed to the side surface 23d on which the chamfered section 23e is formed. For example, when the lid member 23 is detached from the base section 21 during maintenance of the inserting apparatus 100, a tool can be inserted into a gap between the chamfered section 23e and the opening forming surface 21b.

The movable member 51 disposed in the housing space 22 is now explained.

As shown in FIG. 5, FIG. 6, and FIG. 10, the movable member 51 is supported by the base section 21 to be movable with respect to the base section 21 in the first recess portion 21a. Specifically, a bearing 28 piercing through from a bottom surface of the first recess portion 21a to the raising base housing space 20d is formed in the base section 21. The bearing 28 rotatably supports a shaft section 51a fixed to the movable member 51. The movable member 51 includes a lever 51b extending from the shaft section 51a in a direction orthogonal to the shaft section 51a in the first recess portion 21a. Therefore, the lever 51b swings around a rotation axis of the shaft section 51a in the first recess portion 21a.

In the present embodiment, the rotation axis of the movable member 51 is substantially parallel to the X axis. Therefore, the lever 51b moves in a direction generally along the longitudinal axis 2a in the first recess portion 21a (the housing space 22).

A distal end of the raising base operation wire 18 is connected to the lever 51b in a position separated from the shaft section 51a by a predetermined distance. The raising base operation wire 18 is inserted into a through-hole 21d that pierces through the base section 21 and the base portion 20a from a side surface of the first recess portion 21a in the proximal end direction B. Note that, in the present embodiment, a guide pipe 29 that guides the raising base operation wire 18 is inserted into the through-hole 21d. The guide pipe 29 is a rigid tubular member. The raising base operation wire 18 is inserted through the guide pipe 29.

As explained above, the raising base operation wire 18 advances and retracts in a direction along the longitudinal axis 2a according to the swinging of the raising base operation lever 14. Therefore, the lever 51b swings around the rotation axis according to the swinging of the raising base operation lever 14.

The shaft section 51a extends into the raising base housing space 20d. The raising base 50 is fixed to a portion of the shaft section 51a extending into the raising base housing space 20d. Therefore, as shown in FIG. 8, the raising base 50 swings around the rotation axis of the shaft section 51a together with the movable member 51. In other words, the raising base 50 swings around the rotation axis according to the swinging of the raising base operation lever 14.

The raising base 50 is a tongue-like member extending in one direction from the shaft section 51a. The treatment instrument channel tube 17 is opened on the proximal end direction B side of the raising base 50 of the raising base housing space 20d. An angle of the treatment instrument projecting from the treatment instrument channel tube 17 changes according to swinging of the raising base 50.

A part of the lever 51b of the movable member 51 further projects than the opening forming surface 21b from the opening of the first recess portion 21a. In other words, a part of the movable member 51 projects to an inside of the second recess portion 23a formed in the lid member 23.

In other words, in the present embodiment, the movable member 51 moving in the housing space 22 is disposed so as to move substantially in parallel to the mating surface of the base section 21 and the lid member 23. A part of the movable member 51 projects from the first recess portion 21a to the inside of the second recess portion 23a beyond the opening forming surface 21b (the contact surface 23b), which is the mating surface of the base section 21 and the lid member 23. Therefore, when viewed from a direction parallel to the mating surface of the base section 21 and the lid member 23 (for example, when viewed from a visual line direction in FIG. 6), the movable member 51 overlaps the mating surface of the base section 21 and the lid member 23.

A configuration for deciding a moving range of the movable member 51 in the housing space 22 is now explained.

At least one of both ends in the moving range of the movable member 51 in the housing space 22 is decided by a position where the movable member 51 is in contact with a restricting section 22a, which is a part of a sidewall of the housing space 22.

Specifically, in the present embodiment, an end on the distal end direction A side in the moving range of the movable member 51 is a position where the movable member 51 is in contact with the restricting section 22a provided in a part of a sidewall of the first recess portion 21a. FIG. 6 and FIG. 10 show a state in which the movable member 51 is located at the end on the distal end direction A side of the moving range and is in contact with the restricting section 22a.

As explained above, when viewed from the direction parallel to the mating surface of the base section 21 and the lid member 23, the movable member 51 moves in the housing space 22 in a state in which the movable member 51 overlaps the mating surface of the base section 21 and the lid member 23. Accordingly, the restricting section 22a provided on the sidewall of the first recess portion 21a further projects to the proximal end direction B side than a sidewall of the second recess portion 23a in order to come into contact with, earlier than the sidewall of the second recess portion 23a, the movable member 51 moving in the distal end direction A in the housing space 22.

In other words, an opening width in the longitudinal axis 2a direction of the second recess portion 23a is larger than an opening width of the first recess portion 21a. The sidewall of the second recess portion 23a is separated in the longitudinal axis 2a direction from the movable member 51 in a contact state with the restricting section 22a.

By providing, in the base section 21, which is the same member, the bearing 28 that supports the movable member 51 and the restricting section 22a that decides the moving range of the movable member 51 as in the present embodiment, it is possible to improve accuracy of the moving range of the movable member 51. Note that the restricting section 22a may be provided in the lid member 23 (the sidewall of the second recess portion 23a).

On the other hand, an end on the proximal end direction B side in the moving range of the movable member 51 is a position where the raising base 50 fixed to the movable member 51 is in contact with a stopper 20k that projects into the raising base housing space 20d. The stopper 20k is shown in FIG. 5 and FIG. 8. FIG. 8 shows a state in which the raising base 50 is in contact with the stopper 20k. By providing the stopper 20k, which is in direct contact with the raising base 50, in the raising base housing space 20d, it is possible to position the raising base 50 irrespective of fluctuation in fixing positions of the movable member 51 and the raising base 50.

As explained above, the inserting apparatus 100 in the present embodiment includes, in the insertion section 2 inserted into the subject, the housing space 22 for housing the movable member 51. The housing space 22 is configured by the first recess portion 21a formed in the base section 21 provided in the insertion section 2 and the second recess portion 23a formed in the lid member 23 bonded and fixed to the base section 21.

Since thickness of the side surface 23d is larger than thickness in a center of the lid member 23 in the present embodiment, the lid member 23 has high strength. In the present embodiment, the protrusion 30 projecting from the side surface 23d and having a thickness smaller than a thickness of the side surface 23d is provided in the lid member 23. The protrusion 30 is in contact with the wall surface section 21c provided in the base section 21 to thereby position the lid member 23 with respect to the base section 21 and form the groove-like gap 27 having the predetermined width, into which the fixing resin 26 is poured, between the side surface 23d and the wall surface section 21c.

Since the protrusion 30 only projects from a part of the side surface 23d and is a part thinner than the side surface 23d, the groove-like gap 27 continuously extends along the side surface 23d without being cut. Accordingly, in the present embodiment, the fixing resin 26 before curing can be supplied to the entire side surface 23d, which is an outer circumference of the lid member 23.

Therefore, in the inserting apparatus 100 in the present embodiment, during assembly, by curing the fixing resin 26 poured into the gap 27 while bringing the protrusion 30 into contact with the wall surface section 21c, it is possible to firmly fix the lid member 23 while accurately positioning the lid member 23 with respect to the base section 21. As explained above, the inserting apparatus 100 in the present embodiment can improve fixing strength of the lid member 23 that closes the housing space 22 of the movable member 51.

Figure 13:
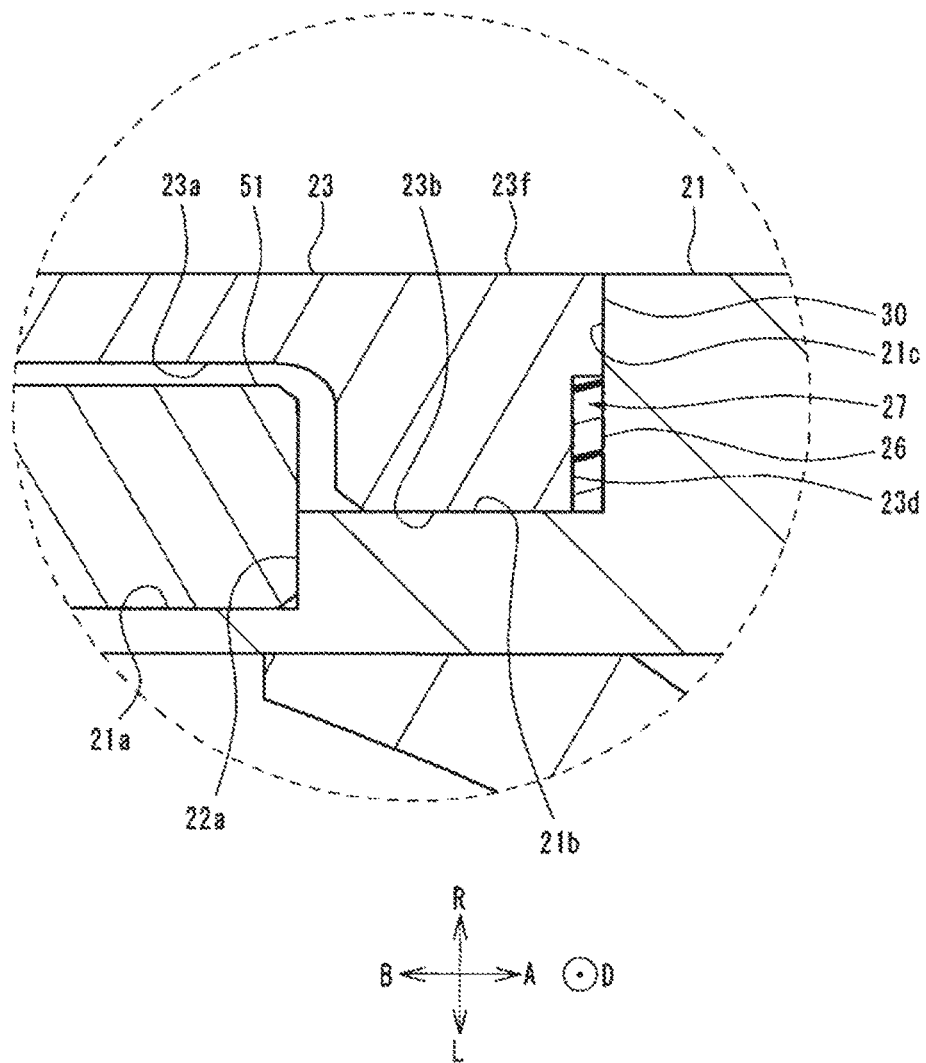
FIG. 13 is a diagram showing a first modification of a protrusion.
Figure 14:
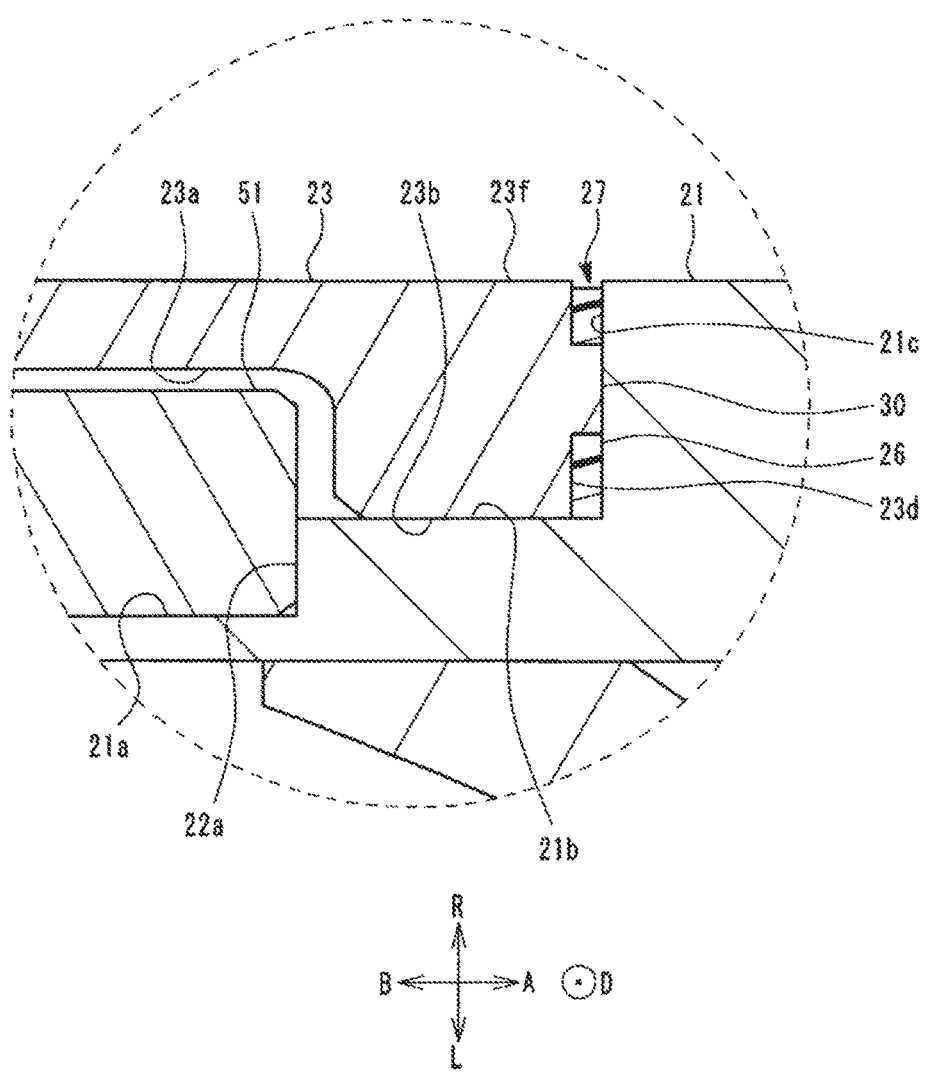
FIG. 14 is a diagram showing a second modification of the protrusion.

Note that, as shown in FIG. 13 as a first modification, the protrusion 30 may be disposed to be separated from the contact surface 23b of the lid member 23. As shown in FIG. 14 as a second modification, the protrusion 30 may be disposed to be separated from both of the contact surface 23b of the lid member 23 and the outer surface 23f. In the modifications shown in FIG. 13 and FIG. 14, in the state in which the contact surface 23b is in contact with the opening forming surface 21b, the groove-like gap 27 is also continuously formed without being cut between the lid member 23 and the wall surface section 21c surrounding the circumference of the lid member 23. Therefore, the same effects as the effects in the embodiment explained above can be obtained in the modifications shown in FIG. 13 and FIG. 14.

Figure 15:
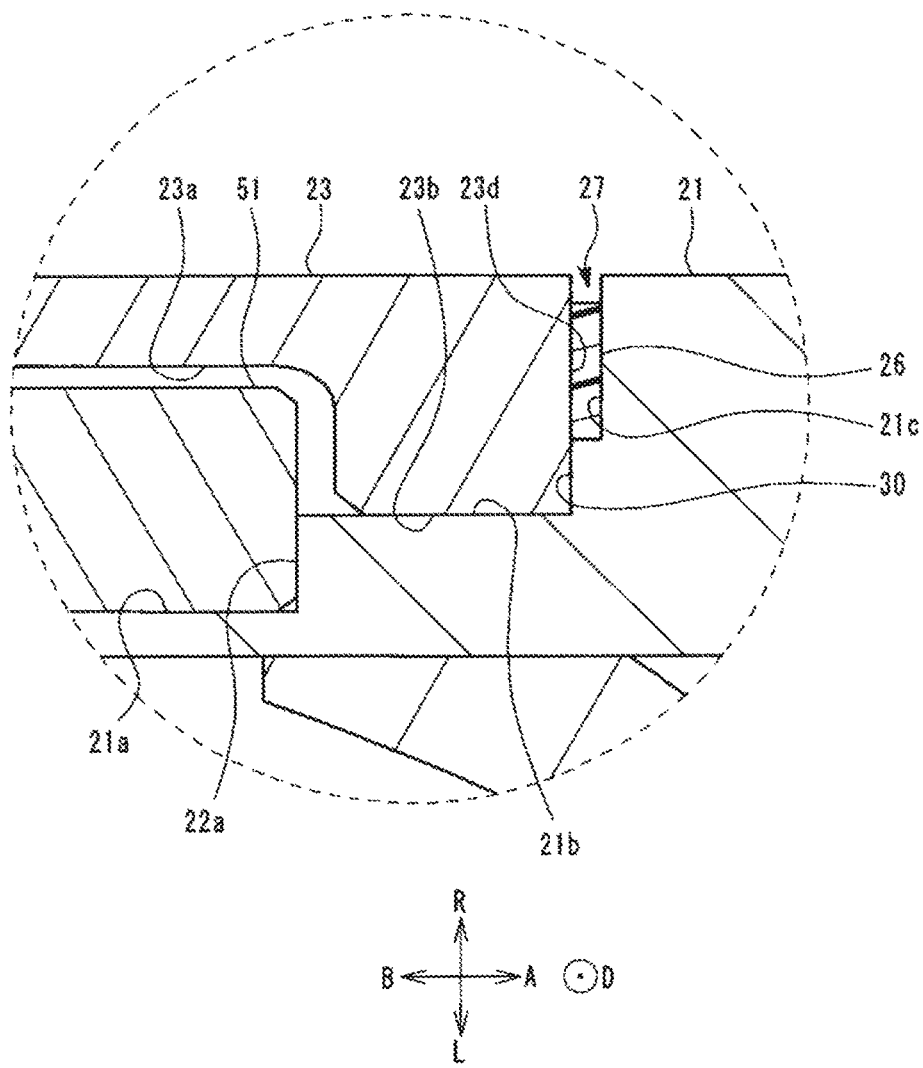
FIG. 15 is a diagram showing a third modification of the protrusion.
Figure 16:
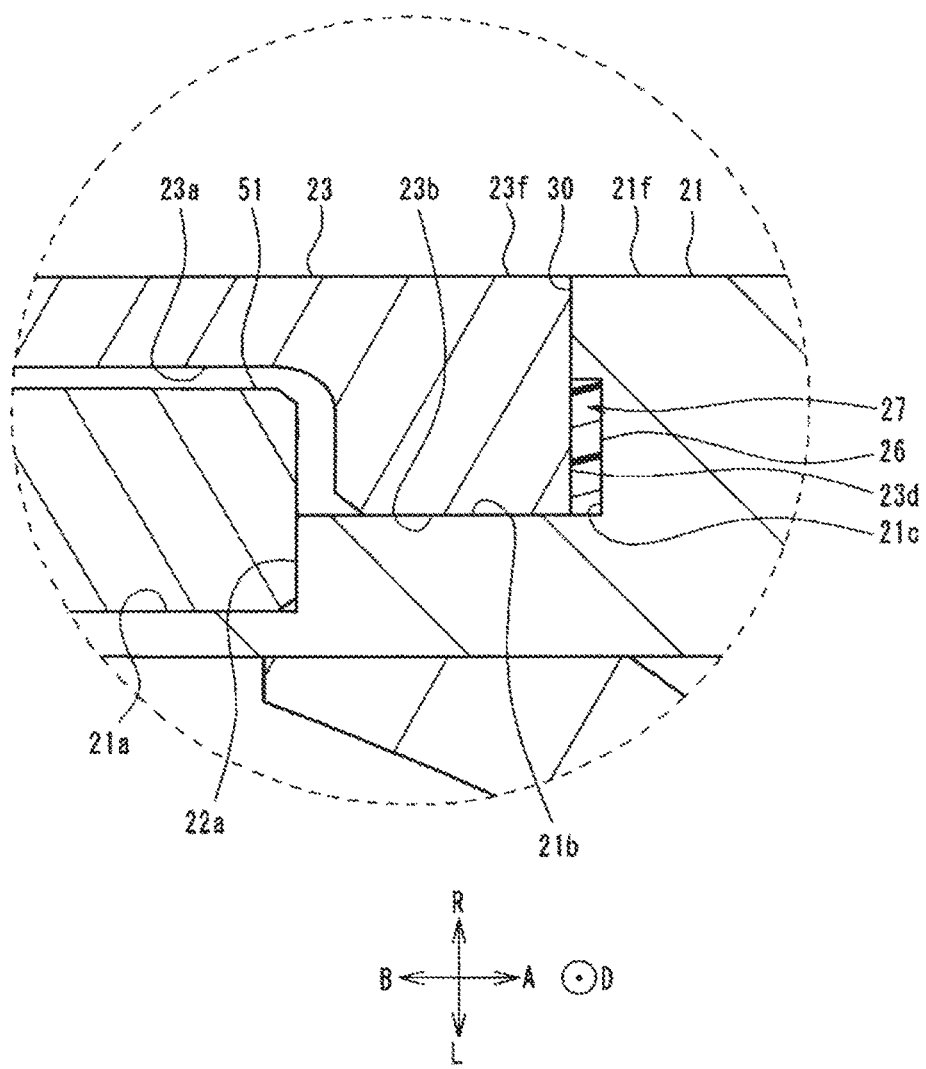
FIG. 16 is a diagram showing a fourth modification of the protrusion.
Figure 17:
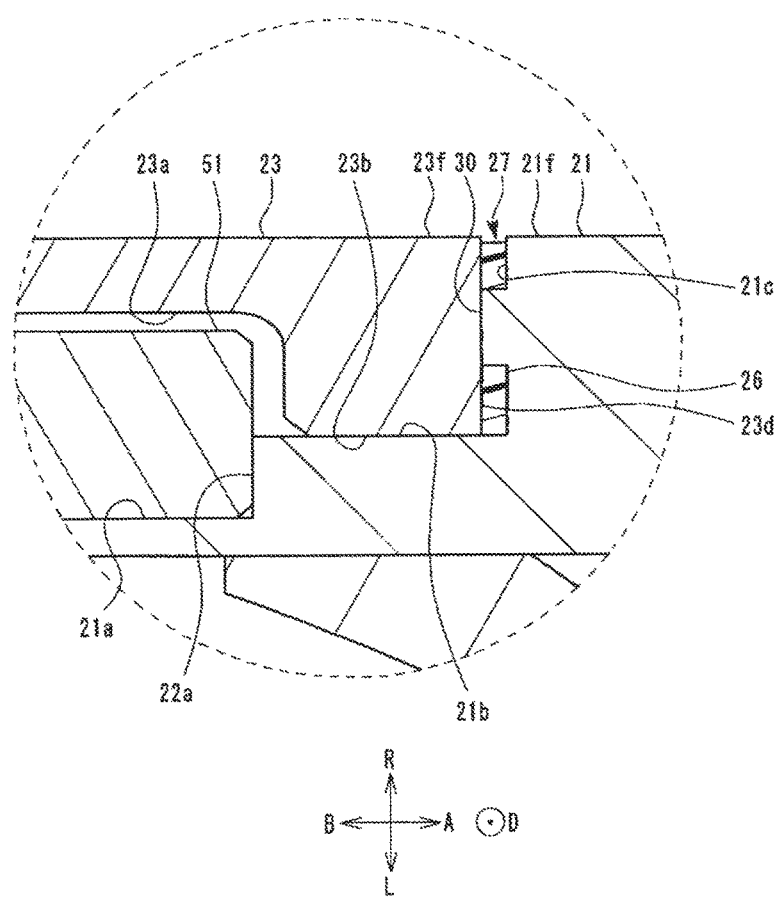
FIG. 17 is a diagram showing a fifth modification of the protrusion.

As shown in FIG. 15 to FIG. 17 as third to fifth modifications, the protrusion 30 may be provided in the wall surface section 21c and project from the wall surface section 21c toward the side surface 23d of the lid member 23. In this case, the protrusion 30 has thickness smaller than the thickness of the side surface 23d of the lid member 23. The protrusion 30 is disposed to be separated in the thickness direction from at least one of the opening forming surface 21b and an end face 21f of the wall surface section 21c. The end face 21f of the wall surface section 21c means a surface of the wall surface section 21c, which projects from the opening forming surface 21b, in a projecting direction. In the present embodiment, the end face 21f is an outer circumferential surface of the base section 21.

In the third modification shown in FIG. 15, the protrusion 30 is disposed to be separated from the end face 21f of the wall surface section 21c. In the fourth modification shown in FIG. 16, the protrusion 30 is disposed to be separated from the opening forming surface 21b. In the fifth modification shown in FIG. 17, the protrusion 30 is disposed to be separated from both of the opening forming surface 21b and the end face 21f. In the modifications shown in FIG. 15 to FIG. 17, in the state in which the contact surface 23b is in contact with the opening forming surface 21b, the groove-like gap 27 is also continuously formed without being cut between the lid member 23 and the wall surface section 21c surrounding the circumference of the lid member 23. Therefore, the same effects as the effects in the embodiment explained above can be obtained in the modifications shown in FIG. 15 to FIG. 17.

The present invention is not limited to the embodiment explained above but can be changed as appropriate in a range not departing from the gist or the spirit of the invention read from the claims and the entire specification. An inserting apparatus involving such a change is also included in the technical scope of the present invention.

What is claimed is:

1. An inserting apparatus comprising:
   a base provided in an insertion section inserted into a subject;
   a first recess recessed on a surface of the base;
   an opening forming surface formed around an opening of the first recess on the surface of the base;
   a movable member configured to move with respect to the base in the first recess, a part of the movable member projecting from the opening of the first recess;
   a tabular lid member including a contact surface larger than the opening of the first recess and in contact with the opening forming surface, the lid member closing the opening of the first recess by the contact surface coming into contact with the opening forming surface;
   a second recess recessed on the contact surface of the lid member, the second recess forming a housing space including the movable member by connecting the second recess to the first recess in a state in which the lid member closes the opening of the first recess;
   a wall surface provided on the base, erected toward an outer side of the base from the opening forming surface, and opposed to at least a part of a side surface of the lid member in a state in which the contact surface is in contact with the opening forming surface;
   a fixing resin disposed at least in a gap between the side surface of the lid member and the wall surface in the state in which the contact surface is in contact with the opening forming surface, the fixing resin fixing the lid member to the base; and
   one or a plurality of protrusions provided in one of the side surface of the lid member and the wall surface, having thickness smaller than thickness in the side surface of the lid member, and projecting from the one of the side surface of the lid member and the wall surface toward another of the side surface of the lid member and the wall surface.

2. The inserting apparatus according to claim 1, wherein
the opening forming surface includes a surface formed on a side surface of the base and extending in a longitudinal axis direction of the insertion section,
the movable member is movable within a predetermined moving range in the longitudinal axis direction with respect to the base,
the wall surface is disposed to hold, in the longitudinal axis direction, the lid member in a state in which the contact surface is in contact with the opening forming surface, and
the plurality of protrusions are disposed to project in both directions of the longitudinal axis direction from the side surface of the lid member.

3. The inserting apparatus according to claim 1, wherein the protrusion is provided in the lid member and disposed to be separated in a thickness direction from an outer surface on an opposite side of the contact surface of the lid member.

4. The inserting apparatus according to claim 1, wherein the protrusion is provided on the wall surface and disposed to be separated in a thickness direction from an end face of the wall surface.

5. The inserting apparatus according to claim 2, wherein
at least one of both ends in the moving range of the movable member is decided by a position where the movable member is in contact with a restricting section that is a part of a sidewall of the first recess, and
an opening width in the longitudinal axis direction of the second recess is larger than an opening width of the first recess, and a sidewall of the second recess is disposed to be separated in the longitudinal axis direction from the movable member in a contact state with the restricting section.

6. The inserting apparatus according to claim 1, wherein
the opening forming surface includes a pair of planes parallel to a longitudinal axis direction of the insertion section and disposed at angles at which the pair of planes cross each other, and
the contact surface of the lid member includes a pair of planes respectively in contact with the pair of planes of the opening forming surface.

7. The inserting apparatus according to claim 1, wherein the inserting apparatus is an endoscope.

8. The inserting apparatus according to claim 1, wherein
the opening forming surface is formed on a side surface of the base in a longitudinal axis direction of the insertion section, and
the wall surface is provided to cross, in the longitudinal axis direction, the lid member in a state in which the contact surface is in contact with the opening forming surface.

9. The inserting apparatus according to claim 1, wherein
the opening forming surface of the base is formed larger than the contact surface of the lid member, and
an entire surface of the contact surface is in contact with the opening forming surface.

10. The inserting apparatus according to claim 1, wherein
the movable member is provided to move in a moving range, the moving range being a predetermined range, with respect to the base, and
at least one of both ends defining the moving range is a part of a sidewall of the first recess in contact with the movable member.

11. The inserting apparatus according to claim 1, wherein a thickness of a part including the contact surface of the lid member is formed greater than a thickness of a center portion forming a bottom surface of the second recess in a direction in which the bottom surface of the second recess extends.

12. The inserting apparatus according to claim 1, wherein the opening forming surface is formed to surround a circumference of an opening of the first recess.

13. An inserting apparatus comprising:
a base provided in an insertion section inserted into a subject;
a first recess recessed on a surface of the base;
an opening forming surface formed around an opening of the first recess on the surface of the base;
a movable member configured to move with respect to the base in the first recess;
a lid member including a contact surface in contact with the opening forming surface, the lid member closing the opening of the first recess;
a second recess provided in the lid member, the second recess covering the movable member when the second recess is connected to the first recess in a state in which the opening of the first recess is closed;
a wall surface provided on the base, erected toward an outer side of the base from the opening forming surface, and opposed to at least a part of a side surface of the lid member;
a fixing resin that fixes the lid member to the base; and
one or a plurality of protrusions provided in one of the side surface of the lid member and the wall surface and projecting from the one of the side surface of the lid member and the wall surface toward another of the side surface of the lid member and the wall surface, wherein
the opening forming surface is formed from a surface formed on a side surface of the base and extending in a longitudinal axis direction of the insertion section,
the movable member moves within a predetermined moving range in the longitudinal axis direction with respect to the base,
at least one of both ends in the moving range is decided by a position where the movable member is in contact with a restricting section that is a part of a sidewall of the first recess, and
an opening width in the longitudinal axis direction of the second recess is larger than an opening width of the first recess, and a sidewall of the second recess is disposed to be separated in the longitudinal axis direction from the movable member in a contact state with the restricting section.

* * * * *